(12) United States Patent
Giannelis et al.

(10) Patent No.: US 9,034,371 B2
(45) Date of Patent: May 19, 2015

(54) FUNCTIONALIZED NAONOSTRUCTURES WITH LIQUID-LIKE BEHAVIOR

(75) Inventors: Emmanuel P. Giannelis, Ithaca, NY (US); Athanasios B. Bourlinos, Athens (GR)

(73) Assignee: Cornell Research Foundation, Inc., Ithaca, NY (US)

( * ) Notice: Subject to any disclaimer, the term of this patent is extended or adjusted under 35 U.S.C. 154(b) by 2212 days.

(21) Appl. No.: 11/660,148

(22) PCT Filed: Aug. 31, 2005

(86) PCT No.: PCT/US2005/031111
§ 371 (c)(1),
(2), (4) Date: Feb. 13, 2007

(87) PCT Pub. No.: WO2006/110166
PCT Pub. Date: Oct. 19, 2006

(65) Prior Publication Data
US 2007/0254994 A1 Nov. 1, 2007

Related U.S. Application Data

(60) Provisional application No. 60/606,413, filed on Sep. 2, 2004.

(51) Int. Cl.
| | | |
|---|---|---|
| *A61K 9/127* | (2006.01) | |
| *C07H 21/00* | (2006.01) | |
| *A61K 9/14* | (2006.01) | |
| *B82Y 30/00* | (2011.01) | |
| *B82Y 40/00* | (2011.01) | |
| *C01B 31/02* | (2006.01) | |
| *C01G 41/00* | (2006.01) | |
| *C09C 1/30* | (2006.01) | |

(52) U.S. Cl.
CPC .......... *C07H 21/00* (2013.01); *A61K 9/143* (2013.01); *B82Y 30/00* (2013.01); *B82Y 40/00* (2013.01); *C01B 31/0206* (2013.01); *C01B 31/0213* (2013.01); *C01G 41/006* (2013.01); *C01P 2004/64* (2013.01); *C09C 1/3063* (2013.01); *C09C 1/3081* (2013.01)

(58) Field of Classification Search
CPC ....................................................... A61K 9/14
See application file for complete search history.

(56) References Cited

U.S. PATENT DOCUMENTS

| | | | | |
|---|---|---|---|---|
| 3,773,110 | A * | 11/1973 | Groves, Jr. ................. | 166/309 |
| 5,925,288 | A * | 7/1999 | Umamori et al. ........... | 252/572 |
| 6,326,104 | B1 | 12/2001 | Caja et al. | |
| 6,462,096 | B1 * | 10/2002 | Dino et al. ................. | 516/101 |
| 2002/0034923 | A1 * | 3/2002 | Bookbinder et al. ....... | 451/37 |

OTHER PUBLICATIONS

Zhu, Z., et al., "Preparation of mesoporous 12-tungstophosphoric . . . ", 2003, Sudies in Surface Science and Catalysis, 146, pp. 649-652.*
Maitra, P., et al. "Poly(ethylene oxide) Silanated . . . ", 2003, Langmuir, 19, pp. 8994-9004.*
Liao, C., et al., "Enhanced Ionic Conductivity . . . " 2003, Journal of Polymer Research, 10, pp. 241-246.*
Leroux, F., et al., :Intercalation of Poly(ethylen oxide) derivatives . . . , 2003, Eur. J. Inorg. Chem., pp. 1242-1251.*
Almaza-Workman, A., et al., 2002, Thin Solid Films, 423, pp. 77-87.*
Sysilia 310 MSDS, 2013.*
Yadav et al, 1-Butyl-3-methylimidazolium Tetrafluoroborate ([Bmim]BF4) Ionic Liquid: A novel and Recyclable Reaction Medium for the Synthesis of vic-Diamines, Advanced Synthesis and Catalysis, 2003, 345(8), 948-952.*
Bourlinos, A.B., et al., "A Liquid Derivative of 12-Tungstophosphoric Acid with Unusually High Conductivity", J. Am. Chem. Soc. 126, 15358-15359, 2004 & Supporting Information.
Bourlinos, A.B., et al., "Surface-Functionalized Nanoparticles with Liquid-Like Behavior", Adv. Mater. 17, No. 2, 234-237, 2005.
Bourlinos, A.B., et al., "Functionalized Nanostructures with Liquid-Like Behavior: Expanding the Gallery of Available Nanostructures", Adv. Funct. Mater. 15, 1285-1290, 2005.
Vaia, R.A., et al., Interlayer Structure and Molecular Environment of Alkylammonium Layered Silicates, Chem. Mater., 1994, 6, (7), pp. 1017-1022.

* cited by examiner

*Primary Examiner* — Paul Dickinson
(74) *Attorney, Agent, or Firm* — Hodgson Russ LLP

(57) ABSTRACT

Compound containing at least 15% inorganic content demonstrates liquid-like behavior and is distinct in exhibiting liquid-like behavior in the absence of solvent. In one case it is quaternary ammonium derivative of a heteropolyacid. In another case, it is a salt formed by reaction of heteropolyacid and polyethylene glycol alkylamine. In other cases, it is condensation product of oxide and quaternary ammonium cation where the balancing anion has a molecular weight greater than 200. In still other cases it is a salt formed by reaction of sulfonated silica or sulfonated fullerene and polyethylene glycol alkylamine. In still other cases, it is a neutral organic-inorganic hybrid which is PEG-functionalized silica nanoparticle or is a layered-nanoparticle obtained by hydrolytic polymerization of organosilane in nonpolar solvent.

15 Claims, No Drawings

FUNCTIONALIZED NAONOSTRUCTURES WITH LIQUID-LIKE BEHAVIOR

CROSS-REFERENCE TO RELATED APPLICATIONS

This application is a 371 National Phase filing of PCT/US2005/031111 filed Aug. 31,2005 which claims the benefit of U.S. Provisional Patent Application 60/606,413, filed Sep. 2, 2004, the whole of which is incorporated herein by reference.

This invention was made at least in part with U.S. Government support under Air Force Office of Scientific Research Contract No. F49620-01-1-0082. The U.S. Government has certain rights in the invention.

TECHNICAL FIELD

This invention relates to ionic liquids based on nanoparticles and nanoclusters, e.g., functionalized inorganic nanoparticles or nanoclusters, e.g., functionalized polyoxometalate, oxide, organosilicate and fullerene nanoparticles or nanoclusters, that demonstrate liquid-like behavior in the absence of solvents.

BACKGROUND OF THE INVENTION

Among the gallery of proton conductors are solid heteropolyacids, e.g., polyoxometalates. However, because they are solid, they are highly sensitive to temperature and humidity.

Moreover known functionalized nanoparticles in the absence of solvent behave solid-like. Solids present environmental concern and require presence of solvents for films and functional fluids.

Furthermore layered organic-inorganic hybrids including nanoclays have potential application as rheology control additives and in nanocomposites. However, they do not reversibly melt (undergo a solid-to-liquid transition) at low temperatures; they are not useful therefore as lubricants, plasticizers or film forming precursors.

In each case, the disadvantage is that a compound with an inorganic component does not undergo solid-to-liquid phrase transition at low temperature, i.e., demonstrate liquid-like behavior at low temperature.

SUMMARY OF THE INVENTION

It has been discovered that inorganic containing compound can be transformed into liquid state in the absence of a solvent. Said liquid can be derived from inorganic compound, e.g., in the form of nanoparticles or nanometer size clusters, which is solid at temperatures below 200° C. (1) by converting the inorganic compound which is solid at temperatures below 200° C. to a salt comprising polyoxyethylene (5-20) and $C_7$-$C_{20}$ alkylamine moieties and preferably also a sulfonate moiety or (2) by forming from the inorganic compound a neutral organic-inorganic hybrid containing polyoxyethylene (5-20) moiety.

A generic invention herein is directed to compound that contains from 15% to 50% by weight inorganic content and 85% to 50% by weight organic content and is distinct in demonstrating (exhibiting) liquid-like behavior in the absence of solvent. The compound demonstrates liquid-like behavior. The compound typically reversibly melts at a temperature below 140° C. at atmospheric pressure.

In one embodiment the compound herein is a salt which also comprises polyoxyethylene (5-20) and $C_7$-$C_{20}$ alkylamine moieties. The salt can be, for example, quaternary ammonium derivative of heteropolyacid or condensation product of quaternary ammonium cation where the balancing anion has a molecular weight greater than 200. The salt can also be reaction product of heteropolyacid and a polyoxyethylene (5-20) $C_7$-$C_{20}$ alkylamine. In a preferred case in respect to compounds derived from inorganic oxides, the compound also contains a sulfonate moiety. In the case of compound which is condensation product of quaternary ammonium cation, the balancing anion can contain the sulfonate moiety. In other cases, the salt can be the reaction product of a sulfonated oxide or a sulfonated fullerene and a polyoxyethylene (5-20) $C_7$-$C_{20}$ alkylamine.

In a second embodiment herein, the compound is a neutral organic-inorganic hybrid which is obtained by reacting neutral organosilane containing polyethylene glycol moiety with colloidal silica to attach the organosilane to silica surface through covalent Si—O—Si bonding and produce polyethylene glycol functionalized silica nanoparticles or a layered organic-inorganic hybrid obtained by hydrolytic polymerization of organosilane, e.g., octadecyltrichlorosilane, in a nonpolar solvent.

In another embodiment of the invention herein, there is provided a method for preparing compound of the first embodiment which comprises converting inorganic containing compound which is solid at a temperature below 200° C. to its quaternary ammonium derivative where the cation and anion portions together contain at least two organic chains where each chain contains at least 15 carbon atoms.

DETAILED DESCRIPTION

We turn now to the generic embodiment of the invention herein.

The compounds are functionalized nanostructures, i.e., functionalized nanoparticles (particles having one dimension less than 50 nm), functionalized nanometer size clusters or functionalized layered structures (layer thickness less than 1 nm). The term "nanostructures" as used herein means, nanoparticles, nanometer size clusters or layered structures with layer thickness less than 1 nm.

As used herein, the term "demonstrating liquid-like behavior" means conductivity following the Vogel-Tammann-Fulcher (VTF) expression and shear loss modulus G" higher than the storage modulus G', e.g., at least one order of magnitude higher than the storage modulus.

As used herein, the term "nanometer size clusters" means a single or multi-component system (e.g., $C_{60}$, binary component system as for iron oxide clusters or ternary component system as for polyoxometalate clusters), e.g., of dimension of about 1 nm to 10 nm or more, usually below 2 nm, where the dimensions may approach the atomic scale where each cluster may contain 2 to 100 or more atoms.

The nanostructure of the compounds herein, is preserved when the compound is in liquid state; what changes from solid to liquid state is the assembly (e.g., disorganization) of the nanoparticles.

We turn now to the case of the first embodiment of the invention herein, i.e., where the compound is a salt.

In some cases, the salt can be, for example, a quaternary ammonium derivative of a heteropolyacid, e.g., a polyoxometalate, e.g., a quaternary ammonium derivative of $H_3PW_{12}O_{40}$ which may be called 12-tungsto phosphoric acid, e.g., a reaction product of a heteropolyacid and a quaternary ammonium compound comprising polyoxyethylene (5-20) and $C_7$-$C_{20}$ alkylamine moieties. In other cases, the salt can be a condensation product of an oxide and quaternary ammonium cation where the balancing anion has a molecular weight greater than 200.

We turn now to a case where the compound is a quaternary ammonium derivative of $H_3PW_{12}O_{40}$ and particularly can be $H_{3-x}S_xPW_{12}O_{40}$ where x is about 2 and S is $(CH_3)(C_{18}H_{37})N^+[(CH_2CH_2O)_nH][(CH_2CH_2O)_mH]$ where n+m is 15; this can be made as described in Working Example I hereinafter. The compound is a viscous, optically transparent liquid at room temperature in the absence of solvent, i.e., neat, contains 57 wt. % inorganic and 43 wt. % organic (determined by weight loss incident to TGA analysis) and exhibits anhydrous proton conductivity four orders of magnitude higher than that of its solid anhydrous analog and super-ionic behavior and is therefore attractive as a solvent/reaction medium, electrolyte and in catalysis. The compound consists of nanometer size molecular structures. The functionalized compounds are present as a nanometer size cluster in both solid and liquid state.

We turn now to the case where the salt is a reaction product of a heteropolyacid, e.g., a polyoxymetalate, and a polyoxyethylene (5-20) $C_7$-$C_{20}$ alkylamine, e.g., polyoxyethylene (15)octadecylamine. A synthesis of the salt is described in Working Example II hereinafter.

We turn now to cases where the salt is an oxide nanoparticle surface functionalized with cationic organosilane and combined with the anion of molecular weight greater than 200, e.g., a condensation product of an oxide and silane containing quaternary ammonium cation where the balancing anion has a molecular weight greater than 200.

In three examples of this, silica nanoparticles (at least one dimension is less than 10 nm; 7 nm diameter particles used) are condensed with $(CH_3O)_3Si(CH_2)_3N^+(CH_3)(C_{10}H_{21})_2Cl^-$ and the chloride counter anion is exchanged with isostearate or asymmetric group, e.g., oleate, or polyethylene glycol containing group, e.g., $C_{13\text{-}15}$alkyl$(OCH_2CH_2)_7O(CH_3)_3SO_3^-$. Synthesis of these is described in Working Example III hereinafter. When chloride is the counter anion, no melting is observed after heating to 150° C., i.e., above the surface decomposition temperature of the organic surface modifier. Turning now to the case where the counter anion is $C_{13\text{-}15}$ alkyl $(OCH_2CH_2)_7O(CH_3)_3SO_3^-$, the expected inorganic content is 27 wt. % and organic content is 73 wt. %, and the compound is a clear liquid at room temperature at atmospheric pressure in the absence of solvent, i.e., neat, and dissolves polar dyes (e.g., methylene blue) and nonpolar dyes (e.g., coumarin derivatives), and dissolves pyrrole to produce a medium for polymerization to polypyrrole. We turn now to the cases where the counterion is isostearate (inorganic content of 50 wt. %) or oleate (inorganic content of 40 wt. %). In the isostearate and oleate cases, the compounds are gel-like at room temperature and melt reversibly at 120° C., leading to low viscosity liquids in the absence of solvent, i.e., neat. The ionic conductivity of the sulfonate salt follows VTF expression at room temperature and the isostearate and oleate analogs exhibit Arrhenious conductivity behavior up to the transition at 120° C., after which a VTF behavior is seen. The shear loss modulus G" for the sulfonate salt is much higher than the storage modulus G' throughout a 50-120° C. range whereas both the isostearate and oleate analogs provide G'>G" up to the melting transition at 120° C. after which G">G'. All these compounds flow in the absence of solvent above their melting transition which in all cases is below 140° C. All these compounds preserve their nanostructure in liquid state (i.e., the core nanoparticles remain intact). The three silica derivatives are useful to dissolve polar and nonpolar dyes and as polymerization media e.g., for polymerization of pyrrole, in the absence of solvent.

In another example where the salt is an oxide nanoparticle surface functionalized with cationic organosilane and combined with anion of molecular weight greater than 200 to produce a salt which is a condensation product of an oxide and a silane containing quaternary ammonium where the balancing anion has a molecular weight greater than 200, iron oxide, e.g., maghemite (gamma-$Fe_2O_3$) nanocrystals (4 nm diameter) are condensed with $(CH_3O)_3Si(CH_2)_3N^+(CH_3)(C_{10}H_{21})_2$ $Cl^-$ and the chloride counter anion is exchanged with $C_{13\text{-}15}$alkyl$(OCH_2CH_2)_7O(CH_3)_3SO_3^-$. Synthesis of this compound is described in Working Example IV hereinafter. While the chloride is a solid and does not melt up to 150° C. (i.e., before decomposition of the organic groups), the sulfonate analog is a viscous liquid at room temperature and flows easily at 40° C. in the absence of solvent, i.e., neat, and the nanostructure is preserved in liquid state. The inorganic content of the sulfonate is 40 wt. %. Transparent coatings of the sulfonate can be deposited easily on different substrates. Magnetic measurements confirm the superparamagnetic nature of the compounds with a saturation magnetization at room temperature of 16 emu per gram of functionalized iron oxide or about 40 emu per gram of gamma-$Fe_2O_3$. The compound is the first example of a superparamagnetic liquid (ferrofluid) in the absence of solvent at a temperature less than 50° C. The superparamagnetic fluid is useful for example for medical imaging.

We turn now to cases where the compound is a salt and contains polyoxyethylene (5-20), $C_7$-$C_{20}$ alkylamine and sulfonate moieties.

One case of this is the case above where silica nanoparticles are condensed with $(CH_3O)_3Si(CH_2)_3N^+(CH_3)(C_{10}H_{21})_2$ $Cl^-$ and the chloride counter anion is exchanged with $C_{13\text{-}15}$ alkyl $(OCH_2CH_2)_7O(CH_3)_3SO_3^-$. Another case of this is the case above where iron oxide nanocrystals are condensed with $(CH_3O)_3Si(CH_2)_3N^+(CH_3)(C_{10}H_{21})_2$ and the chloride counterion is exchanged with $C_{13\text{-}15}$ alkyl $(OCH_2CH_2)_7O(CH_3)_3SO_3^-$.

Other cases of this are the reaction product of sulfonated inorganic containing compound nanoparticles and polyoxyethylene (5-20) $C_7$-$C_{20}$ alkylamine. The sulfonated inorganic containing nanoparticles can be, for example, sulfonated silica nanoparticles or sulfonated fullerene nanoparticles. The reaction can be carried out by adding a water solution of polyoxyethylene (5-20) $C_7$-$C_{20}$ alkylamine, e.g., polyoxyethylene(15)octadecylamine, to a dispersion of sulfonated nanoparticles in water until the pH of the final dispersion is 4.5. The dispersion is then dried until all the water is evaporated whereupon rinsing with water is carried out and the water is evaporated. The resulting material is in liquid form. Sulfonated silica nanoparticles can be produced by neutralizing a solution of 3-(trihydroxysilyl)-1-propanesulfonic acid to pH 7, admixing the neutralized silane with silica nanoparticles at a weight ratio of 1:1, and after reaction, precipitating the product, washing, drying and converting to the acid form. Sulfonated fullerene can be made as described in Chiang, L. Y., et al., Journal of Organic Chemistry 59(14), 3960-3968 (1994). Pertinent syntheses are set forth in Working Examples V and VI hereinafter.

We turn now to the second embodiment of the invention herein where the compound of the invention is a neutral organic-inorganic hybrid.

We turn firstly to a case where neutral organosilane containing polyethylene glycol moiety is reacted with colloidal silica to attach the organosilane to silica surface through covalent Si—O—Si bonding to produce polyethylene glycol functionalized silica nanoparticles.

In an example of this case colloidal silica (particle size 7 nm) is reacted with $(CH_3O)_3Si(CH_2)_3O(CH_2)(CH_2O)_{6-9}CH_3$ to produce PEG functionalized silica nanoparticles. An exemplary synthesis is set forth in Working Example VII. In the reaction, the neutral organosilane directly attaches to silica surface through Si—O—Si bonding. The product compound is a clear liquid at room temperature in the absence of solvent, i.e. neat, and has inorganic content of 40-50% w/w, and the nanostructure is preserved in liquid state. Colored versions can be obtained by dissolving dye molecules in the liquid and then solidifying.

We turn now to a case where a neutral layered organic-inorganic hybrid is obtained by hydrolytic polymerization of organosilane. In an example of this, hydrolytic polymerization of octadecyltrichlorosilane (OTS) is carried out in non-polar solvent, e.g., toluene (e.g., $H_2O/OTS=2:1$ molar ratio). The result is a layered hybrid of solid nanoparticles at room temperature. A synthesis is set forth in detail in Working Example VIII hereinafter. The IR of the hybrid exhibits strong absorption bands below 3000 $cm^{-1}$ and at 1120 $cm^{-1}$ characteristic of aliphatic chains and a siloxane network. The thickness of the particles lies between 10-20 nm, corresponding to an average stacking of 3-9 individual layers with lateral size between 0.1 and 0.3 μm. The powder sample product upon heating undergoes a transition above 55° C. resulting in a highly transparent liquid in the absence of solvent, i.e., neat. Upon cooling the liquid solidifies taking the shape of the container in which it is present. The melting-solidification is reversible. The DSC profile shows a sharp endothermic transition at 53° C. TGA shows organic and inorganic content of 80 wt. % and 20 wt. % respectively, corresponding to a composition that agrees well with the formula $O_{1.5}SiC_{18}H_{37}$ for the ratio of atoms. The material appears solid-like from a G' compared to G" relation (i.e., G'>G") up to about 65° C. after which liquid-like behavior (G">G') is exhibited. At the transition, the viscosity of the sample decreases significantly with values commensurate with a liquid-like state. Unlike the previously reported meltable hybrids, where solidification of the sample is observed after prolonged heating above 100° C., the liquid-like behavior of the material described above, remains unaltered with time at 120° C. While in the solid state, the compound exhibits a multilayer structure of alternating organic-inorganic layers and is dispersible in common organic solvents. The compound's dispersibility, high thermal stability, low vapor pressure and ability to flow at low temperatures, make it attractive for lubricant, plasticizer and film-forming precursor use.

We turn now to the embodiment herein directed to preparing a compound that contains from 15% to 50% by weight inorganic content and 85 to 50% by weight organic content and is distinct in exhibiting liquid-like behavior in the absence of a solvent. The method comprises converting inorganic containing compound which is solid at a temperature less than 200° C. to quaternary ammonium derivative when the cation and anion portions together contain at least two chains which each contains at least 15 carbon atoms. One example of this comprises replacing hydrogen ion of heteropolyacid, e.g., polyoxometalate, e.g., $H_3PW_{12}O_{40}$, with quaternary ammonium cation containing at least two chains each of which contains at least 15 carbon atoms. A detailed example of this is set forth in Working Example I. Another example of this comprises condensing inorganic oxide with a quaternary ammonium compound containing at least one chain containing at least 15 carbon atoms and providing a balancing cation containing at least one chain containing at least 15 carbon atoms. Detailed examples are Working Examples III and IV herein.

The invention is exemplified by the following working examples.

WORKING EXAMPLE I

Synthesis of Liquid $H_{3-x}S_xPW_{12}O_{40}$ Nanoclusters

Five g of the solid heteropolyacid H3PW12O40 (Fisher Scientific) was treated with 5 ml of $(CH_3)(C_{18}H_{37})N^+$ $[(CH_2CH_2O)_nH][(CH_2CH_2O)_mH]$ $Cl^-$ (Akzo Nobel, m+n=15) at 75° C. for 2 h. The solid acid was gradually dissolved by simultaneous evolution of gas according to the reaction: $H_3POM+x\ S^+Cl^- \rightarrow H_3-xS_xPOM+x\ HCl$ where $S^+$ stands for the PEG containing ammonium cation. The clear liquid was extracted several times with a hot toluene/acetone mixture (85:15 v/v) to remove any residual solvent. Finally, the remaining product was carefully washed with water and re-dried at 75° C. for 24 hr to yield the functionalized heteropolyacid as a viscous, optically transparent liquid at room temperature. An aqueous solution of the liquid POM salt has a pH=2 suggesting the presence of residual protons after exchange.

WORKING EXAMPLE II

Synthesis of Liquid Salt From Reaction of Heteropolvacid and Polyethylene Glycol Alkylamine Five g of the solid heteropolyacid (POM) of working Example I was treated with polyoxyethylene(15)octadecylamine (Azko Nobel), 2 amine moles per mole of POM in water. After homogenization, the solvent was allowed to evaporate at room temperature. The product was the salt reaction product of POM and polyoxyethylene(15)octadecylamine and was liquid at room temperature.

WORKING EXAMPLE III

Syntheses of Liquid and Low Temperature Melting Quaternary Ammonium Functionalized $SiO_2$ Nanoparticles 3.5 ml of Ludox colloidal silica (Ludox-SM, 30 wt. % $SiO_2$, particle size: 7 nm, pH=10) were diluted with 20 ml de-ionized water. To the suspension 5 ml of $(CH_3O)_3$ $Si(CH_2)_3N^+(CH_3)(C_{10}H_{21})_2$ $Cl^-$ in methanol (40%, Gelest) were added. The white precipitate formed immediately and was aged for 24 h at room temperature by gently shaking it from time to time. After that, the solvent was discarded and the solid was rinsed three times with water and twice with ethanol. The solid was re-suspended in ethanol, poured into a Petri dish and dried at 70° C. The corresponding sulfonate nanosalt was prepared by treating 1 g of the chloride analog with 15 ml of a 10.5 w/v % solution of $R(OCH_2CH_2)_7$ $O(CH_2)_3SO_3^-K^+$ (R: $C_{13}$-$C_{15}$ alkyl chain, Aldrich) in water at 70° C. for 24 h. Following removal of the solution, the material was washed several times with water and dried at 70° C. The isostearate and oleate salts were prepared similarly by ion-exchanging the chloride with isostearate and oleate salts, respectively, except using a 6.6 w/v % solution of caroboxylate salt. The products are described above.

The synthesized compound with sulfonate counter anion is admixed with 0.01 wt. % methylene blue at room temperature and a solution is formed.

The synthesized compound with sulfonate counter anion is admixed with 10 wt. % pyrrole to form a solution. Polymerization of the pyrrole to polypyrrole is carried out by heating the solution for 48 hours at 100° C.

WORKING EXAMPLE IV

Synthesis of Liquid Quaternary Ammonium Functionalized Iron Oxide Nanoparticles Maghemite ($\gamma$-$Fe_2O_3$) nanocrystals (4 nm) were first prepared by adding 5 ml of concentrated ammonia (28-30%) to 15 ml of ethanol solution containing 6 g $Fe(NO_3)_3$-$9H_2O$ under vigorous stirring. The as-formed iron hydroxide precipitate was centrifuged, washed well with water and air-dried. 2 g of the freshly prepared iron hydroxide were suspended in 40 ml ethylene glycol and the suspension was purged with flowing argon prior to refluxing under an argon atmosphere for 1 h. After reaction, the admixture was cooled to room temperature, centrifuged and washed first with acetone followed by water. The solid was re-suspended in acetone and air-dried.

The maghemite nanosalts were prepared by first dispersing 0.5 g of $\gamma$-$Fe_2O_3$ in 10 ml of alkaline $H_2O$ (pH=10, $NH^4OH$) and sonicating the suspension for 25 min in a warm bath followed by the addition of 3 ml of the silane solution. The precipitate was aged for 24 h at room temperature, filtered and washed repeatedly with water and methanol and dried. The dried solid was dissolved in tetrahydrofuran and left undisturbed for 10 min for settling down any insoluble particles. The clear brown supernatant liquid was evaporated to leave behind the maghemite chloride nanosalt. The sulfonate derivative was prepared similarly to the silica analog by ion exchange with $R(OCH_2CH_2)_7O(CH_2)_3SO_3^-K^+$. After exchange, the waxy brown material obtained was washed with water and dried at 70° C. to produce a viscous liquid.

WORKING EXAMPLE V

Liquid Sulfonated Silica Nanoparticles Derivative

A solution of 3-(trihydroxysilyl)-1-propanesulfonic acid is first neutralized with sodium hydroxide to pH-7. The neutralized silane is then mixed with silica nanoparticles at a 1:1 ratio by weight (LUDOX® SM-30 colloidal silica, average diameter 7 nm). After reaction at 80° C. for 24 hrs the product is precipitated in ethanol, washed 3 times with ethanol and then dried under vacuum at 40° C. The powder is redispersed in water and passed 3 times through a column packed with a cation exchange resin in the proton form to obtain the acid form. To a dispersion of acid form is added a water solution of Ethomeen® 18/25 (polyoxyethylene(15)octadecylamine) until the pH of the final dispersion is 4.5. The dispersion is then dried at 80° C. until all the water is evaporated. The resulting product is rinsed with water and dried at 80° C. The resulting material is in liquid form.

WORKING EXAMPLE VI

Liquid Sulfonated Fullerene Derivative

Sulfonated fullerene is produced by the method described by Chiang, L. Y., et al., Journal of Organic Chemistry 59(4), 3960-3968 (1994). To a solution of the sulfonated fullerene is added a water solution of Ethomeen® 18/25 (polyoxyethylene(15)octadecylamine) until the pH of the final dispersion is 4.5. The dispersion is then dried at 80° C. until all the water is evaporated. The resulting product is rinsed with water and dried at 80° C. The resulting material is in liquid form.

WORKING EXAMPLE VII

Synthesis of Liquid Neutral PEG-Functionalized Silica Nanoparticle

In 3.5 mL of colloidal silica (Ludox SM, 34 wt. % $SiO_2$, 7 nm, pH=10) diluted with 20 mL $H_2O$, 2.5 g of $(CH_3O)_3Si(CH_2)_3O(CH_2CH_2O)_{6-9}CH_3$ (90%, Gelest) were placed. The sol was placed in a sealed plastic bottle and heated at 70° C. there for 24 h. After completion of the reaction, the clear solution was extracted several times with 60 mL of toluene (6-7 times). After extraction, the aqueous layer was isolated and dried at 70° C. to one fifth of its volume (solidification of the concentrate was avoided). The remaining liquid was further extracted with toluene. The as-obtained liquid was dissolved in 10 mL of acetone and centrifuged in order to remove any insoluble particles. The supernatant dispersion was collected and dried at room temperature for 2-3 days followed by 2-3 days vacuum drying to finally produce a clear liquid (organic content 40-50% w/w) denoted Silpeg 7. The liquid is soluble in water, acetone and tetrahydrofuran (THF). When 12 nm silica nanoparticles are substituted for the 7 nm particles, a liquid is obtained (43% w/w organic content), quite comparable in behavior to Silpeg 7. When 22 nm silica particles are substituted for the 7 nm particles, a gel-like product (about 40% w/w organic) is obtained that does not flow or melt up to 140° C. From these results, it is expected that the smaller the inorganic particle size, the higher the fluidity of a product with comparable organic content.

WORKING EXAMPLE VIII

Synthesis of Neutral Organic-Inorganic Hybrid Nanoparticles/from Octadecyltrichlorosilane (OTS)

4 g of OTS were dissolved in 20 ml toluene in a well-dried flask and 0.38 ml of $H_2O$ were added ($H_2O$/OTS-2:1 molar ratio). The mixture was refluxed for 24 h, whereupon a transparent dispersion was obtained. After completion of the reaction, 40 ml of methanol were added to the dispersion and the precipitate was copiously washed with methanol before drying at 70° C. The crude product was dissolved in 10 ml of hot toluene, followed by centrifugation to separate any insoluble products. After separation of the supernatant liquid, 10 ml of methanol were added and the precipitate was again isolated by centrifugation and dried at 70° C. The resulting solid was ground into a powder washed with acetone and dried.

Characteristics of the product are described above.

Variations

The forgoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A functionalized nanoparticle that contains from 15% to 50% by weight inorganic content and exhibits liquid-like behavior in the absence of solvent, and wherein the functionalized nanoparticle exists in a liquid state in the absence of solvent at a temperature below 140° C. and at atmospheric pressure.

2. The functionalized nanoparticle of claim 1 which is a salt.

3. The functionalized nanoparticle of claim 2, further comprising polyoxyethylene (5-20) and $C_7$-$C_{20}$ alkylamine moieties.

4. The functionalized nanoparticle of claim 2, wherein the functional nanoparticle comprises an oxide nanoparticle surface functionalized with a cationic organosilane and combined with an anion of molecular weight greater than 200.

5. The functionalized nanoparticle of claim 4, wherein the functionalized nanoparticle comprises a silica nanoparticle condensed with $(CH_3O)_3Si(CH_2)_3N^+(CH_3)(C_{10}H_{21})_2Cl^-$ where the chloride counterion is exchanged with isostearate or oleate or $C_{13-15}$alkyl $(OCH_2CH_2)_7O(CH_2)_3SO_3^-$.

6. The functionalized nanoparticle of claim 3, wherein the functionalized nanoparticle comprises a sulfonate moiety.

7. The functionalized nanoparticle of claim 6, wherein the functionalized nanoparticle comprises a silica nanoparticle condensed with $(CH_3O)_3Si(CH_2)_3N^+(CH_3)(C_{10}H_{21})_2Cl^-$ where the chloride counterion is exchanged with $C_{13-15}$ alkyl $(OCH_2CH_2)_7O(CH_2)_3SO_3^-$.

8. The functionalized nanoparticle of claim 6, wherein the functionalized nanoparticle is an iron oxide nanoparticle condensed with $(CH_3O)_3Si(CH_2)_3N^+(CH_3)(C_{10}H_{21})_2Cl^-$ where the chloride counterion is exchanged with $C_{13-15}$ alkyl $(OCH_2CH_2)_7O(CH_2)_3SO_3^-$.

9. The functionalized nanoparticle of claim 8, wherein the functionalized nanoparticle is a super paramagnetic liquid in the absence of solvent at a temperature less than 50° C.

10. The functionalized nanoparticle of claim 6, wherein the functionalized nanoparticle comprises a sulfonated silica nanoparticle condensed with polyoxyethylene(15)octadecylamine.

11. The functionalized nanoparticle of claim 1, wherein the functionalized nanoparticle is an organic-inorganic hybrid obtained by reacting neutral organosilane containing a polyethylene glycol moiety with colloidal silica to attach the organosilane to a silica surface through covalent Si—O—Si bonding and produce polyethylene glycol functionalized silica nanoparticles.

12. The functionalized nanoparticle of claim 10 where the neutral organosilane is $(CH_3O)_3Si(CH_2)_3(CH_2O)_{6-9}CH_3$.

13. The functionalized nanoparticle of claim 1, wherein the functionalized nanoparticle is a layered organic-inorganic hybrid obtained by hydrolytic polymerization of organosilane, in nonpolar solvent.

14. A method for preparing the functionalized nanoparticle of claim 1, comprising the step of converting inorganic containing compound which is solid at a temperature below 200° C. to quaternary ammonium derivative where the cation and anion portions together contain at least two chains which each contain at least 15 carbon atoms.

15. The method of claim 14 where the inorganic solid is an oxide which is condensed with a quaternary ammonium compound containing at least one chain containing at least 15 carbon atoms and providing a balancing cation containing at least one chain containing at least 15 carbon atoms.

* * * * *